US00PP24094P3

(12) United States Plant Patent
Maillard et al.

(10) Patent No.: US PP24,094 P3
(45) Date of Patent: Dec. 17, 2013

(54) NECTARINE TREE NAMED 'NECTAFUN'

(50) Latin Name: ***Prunus persica* L. Batsch**
Varietal Denomination: NECTAFUN

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 30 days.

(21) Appl. No.: 13/385,652

(22) Filed: Feb. 29, 2012

(65) Prior Publication Data

US 2012/0227145 P1 Sep. 6, 2012

(30) Foreign Application Priority Data

Mar. 2, 2011 (QZ) ..... PBR 20110559

(51) Int. Cl.
*A01H 5/00* (2006.01)

(52) U.S. Cl.
USPC ..... Plt./190

(58) Field of Classification Search
USPC ..... Plt./190
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of yellow nectarine tree, denominated 'NECTAFUN', has fruits with high eating quality and very long shelf life without alteration before and after harvesting, with a semi-sweet orange yellow flesh, with red pigmentation, and an attractive luminous skin with a high percentage of red blush on skin surface. Fruits can be consumed crunchy or melting.

4 Drawing Sheets

Botanical classification: *Prunus persica* L. Batsch.

Variety denomination: 'NECTAFUN'.

This application claims priority of Community plant variety right No. 2011/0559 filed on Mar. 2, 2011, which is hereby incorporated by reference in its entirety.

BACKGROUND OF THE NEW VARIETY

The present invention relates to a new and distinct variety of yellow nectarine tree, *Prunus persica* L. Batsch, which has been given the variety denomination 'NECTAFUN'. This new tree produces fruit with a long shelf life without alteration both on the tree after growth completion and after harvesting, very good eating quality, clingstone yellow flesh fruit for fresh market in July in the Pyrénées-Orientales department, France. Contrast is made to 'Nectavista (U.S. Plant Pat. No. 21,139), a yellow nectarine variety, and to its parents, 'Nectaprima' (U.S. Plant Pat. No. 17,583) yellow nectarine tree and 'Nectalady' (U.S. Plant Pat. No. 17,580) yellow nectarine tree, for reliable description. 'NECTAFUN' is a promising candidate for commercial success in that it has very attractive fruits with very long shelf life without alteration before after harvesting.

ORIGIN OF THE VARIETY

The 'NECTAFUN' yellow nectarine tree originated in a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'NECTAFUN' variety resulted from a pollinated cross between the 'Nectaprima' (U.S. Plant Pat. No. 17,583) yellow nectarine tree, which was used as the seed parent, and the 'Nectalady' (U.S. Plant Pat. No. 17,580) yellow nectarine tree, which was used as the pollen parent. 'NECTAFUN' was provisionally designated, tested and genetically identified by a genetic profile, under number 01.29W.11 NJ ASF 0704 and was registered at the Official Catalogue of the Agriculture Ministry of the French Republic on Nov. 23, 2010 under number 4047118. The 'NECTAFUN' variety was obtained by hybridizing and propagated by grafting on a 'Franc Inra Montclar' (non-patented) rootstock. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of nectarine tree blooms at the end of February or early in March in the Pyrénées-Orientales department, France. More particularly, it blooms between February 19$^{th}$ and March 10$^{th}$, generally together with 'Nectavista' (U.S. Plant Pat. No. 21,139).

The first fruit of 'NECTAFUN' nectarine tree ripens at the end of June or early in July, generally about 4 or 5 days before 'Nectavista' (U.S. Plant Pat. No. 21,139). More particularly, it approximately ripens between June 15$^{th}$ and July 5$^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
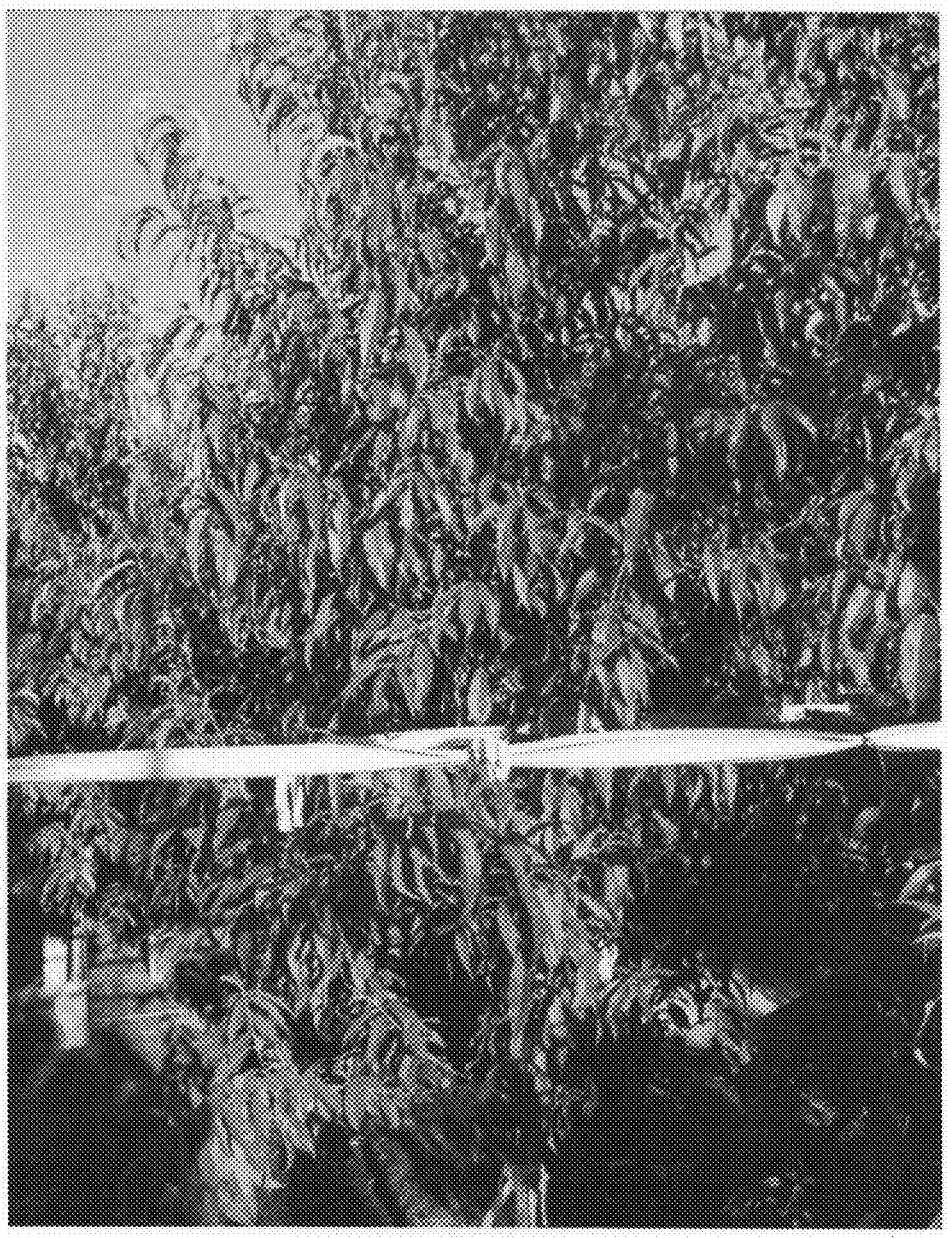
FIG. 1 is a color photograph, which shows a view of a tree of the new variety in orchard, bearing fruits.
Figure 2:
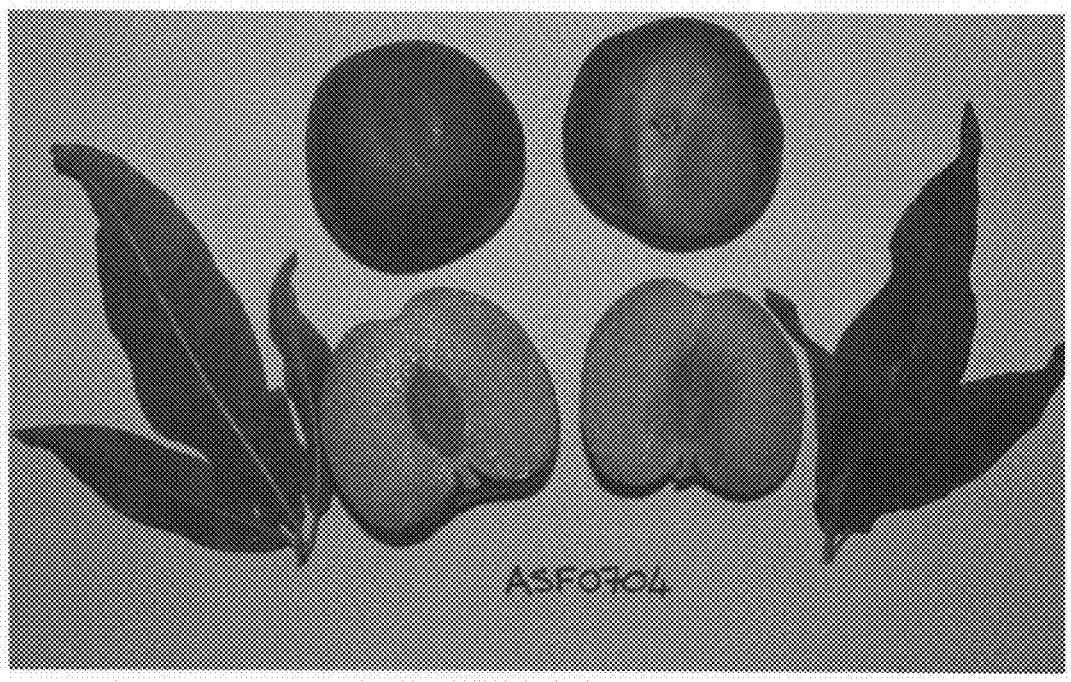
FIG. 2 is a color photograph, which shows two whole fruits and leaves of the new variety, and a third fruit, cut in half, with the stone removed from its cavity, for depicting the fruit flesh of the new variety.
Figure 3:
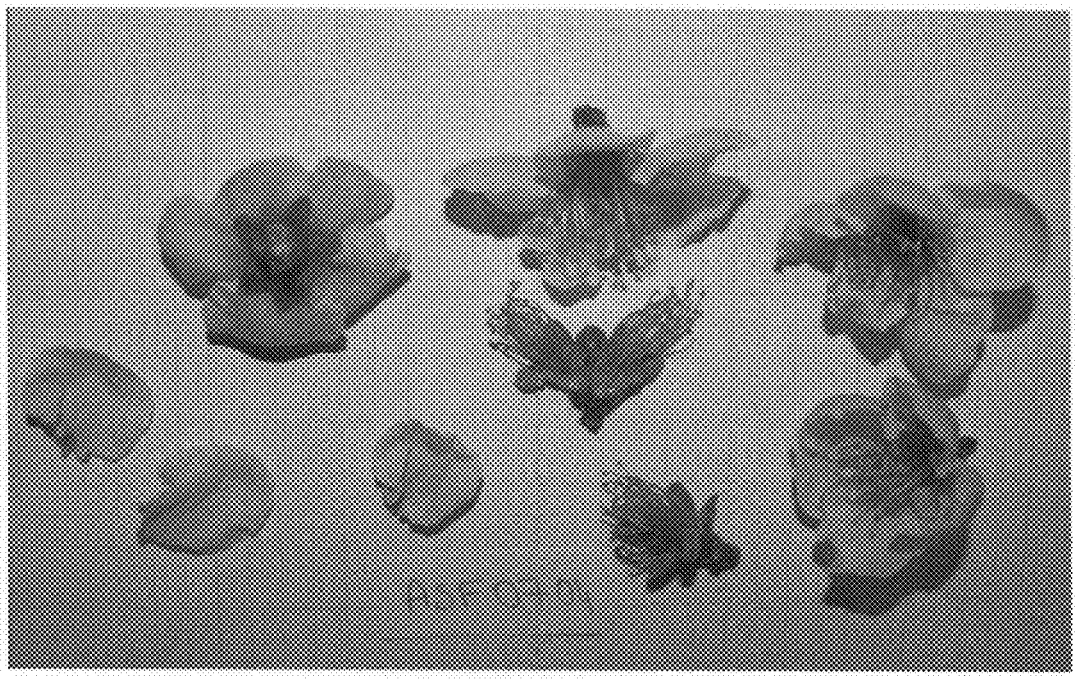
FIG. 3 is a color photograph with reverse and side views of flowers of the new variety, and, with petals removed, reproductive organs of the new variety.
Figure 4:
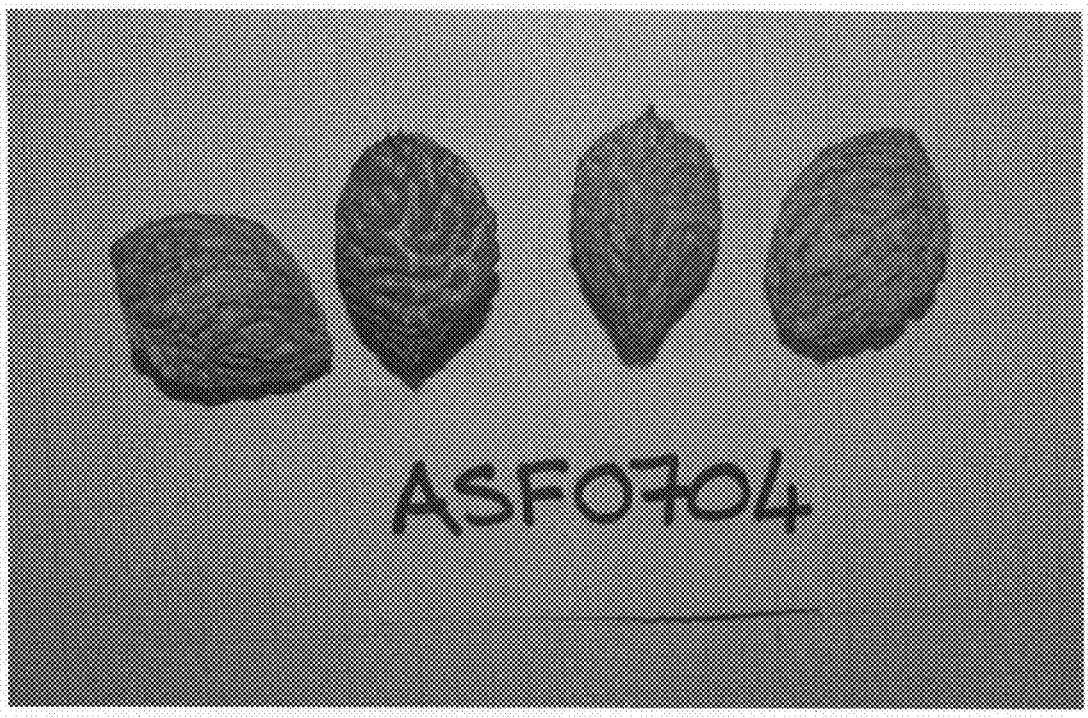
FIG. 4 is a color photograph, which shows different views of the pit.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'NECTAFUN' is high, due to fruit very long shelf life without alteration after harvesting.

Trees are vigorous and large stature half-standing in a semi-flared to semi-upright out aspect. The anthocyanic coloration of flowering shoot is present excluding brushwood side away from sun. The time of beginning of flowering is considered medium; flowering begins at the end of February or early in March. The type of flower is showy with large petal size. Petals are medium pink. Leaf glands are present and reniform. The fruit flesh is yellow to orange and its skin is very thick, with a luminous red blush on an orange background. The stone size is medium. Fruit taste is semi-sweet, very aromatic and with a high level of sugars.

Compared to 'Nectavista' (U.S. Plant Pat. No. 21,139) yellow nectarine tree, 'NECTAFUN' variety blooms approximately at the same time but has an earlier time of maturity, as set forth above. However, 'NECTAFUN' fruits are more luminous than 'Nectavista' fruits, with their purple red coloration, covering 80 to 90% of the fruit surface, on an orange red background.

The new variety male parent, which is 'Nectalady' (U.S. Plant Pat. No. 17,580), produces yellow nectarines. 'Nectalady' comparatively ripens early in September, a few weeks later than the new variety, which ripens in June or early in July. It was chosen as a genitor because of its regular and important fruits productivity and its interesting semi-sweet and aromatic fruits with very high gustative quality.

The new variety female parent, which is the 'Nectaprima' (U.S. Plant Pat. No. 17,583) variety, produces yellow nectarines early in June, approximately 3 weeks earlier than 'NECTAFUN'. 'Nectaprima' was chosen as a genitor because of its regular fruits productivity. The fruits of 'Nectaprima' have very high gustative qualities, with a semi-sweet and aromatic taste. They are very attractive and homogenous in presentation, with their circular form and their luminous orange red coloration.

DETAILED DESCRIPTION

Referring more specifically to the pomological details of this new and distinct variety of yellow nectarine tree, the following was observed on trees in their third growing season (second year of production) under the ecological conditions prevailing at the orchards located near the town of Elne, Pyrénées-Orientales department, France. All observations have been done on rootstock cultivars. Used rootstocks were 'Franc Inra Montclar' (non-patented) trees. All major color code designations are by reference to The R.H.S. Color Chart (Fourth Edition) provided by The Royal Horticultural Society of Great Britain.

TREE

Size:

*Generally.*—Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm with current season shoots length comprised. The tree size is consistently reduced to 250 cm the next years.

Spread: Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

Vigor: Considered vigorous or medium vigorous.

Productivity: Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

Bearer: Very regular. The fruit distribution is considered homogenous on mixed branches and spurs having more than 1 year. Thinning of 1 fruit out of 3 or more was necessary for the tree valorisation. Thinning was necessary every year during the years of observation.

Form: The 'NECTAFUN' variety has naturally a semi-flared to semi-upright shape.

Density: Considered dense.

Hardiness: The present tree was grown and evaluated in France. The variety appears to be hardy under the central Pyrénées-Orientales department typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

TRUNK

Diameter: Approximately between 10.0 cm and 11.0 cm in diameter when measured at a distance of approximately 20 cm above the soil level.

Bark texture: Considered rough, with lenticels.

Lenticels: Numerous lenticels are present. The lenticels range in size from approximately 3.0 millimeters to 7.0 millimeters in width, and from 2.0 millimeters in height.

Lenticel color: The outside of lenticels has a silver-grey color (RHS Grey 201 C), whereas the inside is considered brown (RHS Greyed Orange 165 B to 165 C).

Bark coloration: The bark has a light brown color (RHS Brown 200C) to a silver-grey color (RHS Grey 201 B to 201 C).

BRANCHES

Size: Mature branches and current season shoots are considered medium to large for the variety. Mature branches are pruned to a length of about 50.0 centimeters.

Diameter: Average as compared to other nectarine varieties. The current season shoots have a diameter from 4.0 to 6.0 millimeters, and mature branches have a diameter about 32.0 millimeters.

Surface texture: Average, wood which is several years old has no furrowed appearance.

Crotch angles: Primary branches are considered variable, but the crotch angles are generally between 60 degrees and 75 degrees from the horizontal axis. This particular characteristic is not considered distinctive of the variety, however.

Current season shoots:

*Surface texture.*—Substantially glabrous.

Internode length: Generally 25.0 millimeters to 30.0 millimeters.

Color of mature branches: Medium brown (RHS Grey Brown 199 A to 199 B).

Current seasons shoots:

*Color.*—The color of new shoot tips is considered a light yellow-green (RHS Yellow Green 144 A to 144 B) on lower part of new shoot tips, whereas the upper part is colored in more or less brown-purple (RHS Greyed Purple 187 A to 187 B).

LEAVES

Size: Considered medium to large for the species. The ratio leaf length/leaf width is 3.5.

Leaf length: Approximately 170.0 to 205.0 millimeters with leaf petiole. The medium length is 179.0 millimeters.

Leaf width: Approximately 42.0 to 63.0 millimeters. The medium width is 51.0 millimeters.

Leaf base shape: Concave.

Leaf form: Lanceolate.

Leaf tip form: Acuminate.

Leaf color:

*Upper leaf surface.*—Dark Green (RHS Green 147 A).

*Lower surface.*—A lighter green (RHS Green 147 B) than the upper leaf surface color.

Leaf texture: Smooth and glabrous.

Leaf venation: Pinnately veined.

Mid-vein:

*Color.*—Light green, almost yellow (RHS Yellow Green 150 D). The color may change with maturity.

Leaf margins: Slightly undulating.

Form: Considered slightly dentate.

Uniformity: Leaves are isolated or grouped by 2 or 3. In this last case, one leaf of normal size is found with one or two smaller leaves (at least 50% smaller).

Leaf petioles:

*Size.*—Considered medium to long.

*Length.*—About 10.0 to about 15.0 millimeters.

*Diameter.*—About 1.5 millimeters.

Petioles color:

*Upper petiole surface.*—Light green (RHS Yellow Green 144 B to 144 C).

*Lower surface.*—Light green (RHS Yellow Green 150 C).

Leaf glands:

*Size.*—Considered small. Their length is about 1.0 millimeter and their width is about 1.0 millimeter.

*Number.*—Generally 2 glands per leaf.

*Type.*—Reniform.

*Color.*—On young leaves, leaf gland color is considered a pale green (RHS Yellow Green 145 B). On older leaves, leaf gland color turn to brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variable dimensions. Just before blooming, floral buds are approximately 10.0 millimeters wide and approximately 18.0 millimeters long.

*Color.*—This characteristic is dependent upon the proximity to bloom. At pre-floral stage of development, the bottom of the flowers buds, formed by the sepals, is of purple-brown color (RHS Greyed Purple 183 B to 183 C or Grey Brown Group 199 A); the corolla, formed by the petals, is generally of pale pink color (RHS Red Purple 65 B to 65 C). Petals color shows an evolution until the end of flowering.

Hardiness: The buds are considered hardy under typical central Pyrénées-Orientales department climatic conditions. No winter injury was noted during the last several years of evaluation in the central Pyrénées-Orientales department, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally end of February to beginning of March. The first bloom was observed on Feb. 27, 2003.

Blooming time: Considered medium-season in relative comparison to other commercial nectarine cultivars grown in the Pyrénées-Orientales department, France. The date of full bloom is observed in March, at the middle of the blooming period. The date of bloom varies slightly with climatic conditions and cultural practices. Thus the first full bloom was observed on Feb. 27, 2003. Last observed blooming times were Mar. 1, 2007 then Feb. 19, 2008, then Feb. 26, 2009, then Mar. 10, 2010, then Feb. 23, 2011.

Duration of bloom: Between 10 and 15 days. This characteristic varies slightly with the prevailing climatic conditions.

Flower type: The variety is considered to have a showy type flower.

Flower size: Considered large. Flower diameter at full bloom is approximately 35.0 to 43.0 millimeters.

Bloom quantity: Considered abundant, approximately 45 flowers per meter, with a good distribution and a high rate of fruit set.

Flower bud frequency: Generally 2 flower buds appear per node, occasionally 1.

Petal size:

*Generally.*—Considered large.

Length: Generally about 22.0 millimeters.

Width: Generally about 21.0 millimeters.

Petal form: Round-shaped.

Petal count: Generally 5.

Petal texture: Smooth, sweet and glabrous.

Petal color: Generally, both sides of petals are colored in a medium Pink (RHS Red Purple 65 B to 65 C) when young, becoming slightly darker until the end of blooming.

Fragrance: Sweet.

Petal claw:

*Form.*—The claw is considered to have a truncated form.

*Length.*—Approximately 1.6 to 2.0 millimeters.

*Width.*—Approximately 1.2 to 1.4 millimeters.

*Color.*—A darker pink than the petal color (RHS Red Purple 66 B to 66C).

Petal margins: Generally very slightly wavy, sinuate.

Petal apex:

*Generally.*—The petal apices are generally wide dome-shaped.

Flower pedicel:

*Length.*—Considered medium to large and having an average length of approximately 3.0 to 5.0 millimeters.

*Diameter.*—Considered average, approximately 2.0 millimeters.

*Color.*—A brown to light brown (RHS Grey Brown N199 B to 199 C).

Calyx:

*Internal surface texture.*—Smooth and glabrous.

*Color.*—Generally, both surfaces of the calyx are colored in a matt purple brown (RHS Greyed Purple 183 B to 183 C or RHS Grey Brown 199A) color. Nevertheless, the inner surface of the calyx may be colored in a matt and considered golden-orange (RHS Greyed Red 178 C to 178 D) and the outer surface of the calyx may be considered of purple-brown (RHS Greyed Purple 183 B to 183 C) color.

Sepals:

*Number.*—Generally 5.

*Surface texture.*—The outer surface has a short, fine pubescent texture.

*Size.*—Average.

*Length.*—Approximately 5.0 to 6.0 millimeters.

*Width.*—Approximately 4.0 to 5.0 millimeters.

*Form.*—Ovate.

*Color.*—Generally, both surfaces of sepals are colored in a Matt purple brown (RHS Greyed Purple 183 B to 183 C or RHS Grey Brown 199A). However, the upper face of the sepals sometimes shows a matt and considered golden-orange (RHS Greyed Red 178 C to 178 D) color, whereas the lower surface of sepals is considered of purple-brown (RHS Greyed Purple 183 B to 183 C) color.

*Margins.*—Smooth.

*Apex.*—The apex is round-shaped to emarginated.

Average number of stamens per flower: Approximately 40 stamens per flower.

Anthers:

*Generally.*—Small in length.

*Color.*—Red to orange-red color (approximately RHS Greyed Red 178 A Group). The color may evolve with maturity.

Pollen production: Pollen is abundant, and has a yellow color (Approximately RHS Yellow Orange 17 B to 17 C) which may evolve with maturity. The present variety is considered auto-fertile (self-pollinating).

Filaments:

*Size.*—Medium length, between 11.0 and 18.0 millimeters in length. Filaments length is generally equal to the pistil's length, if not slightly superior.

Color: Considered light pink (approximately RHS Red Purple 62 C to 62 D or RHS Red Purple 73 A to 73 B). The color evolves during the blooming.

Pistil:

*Number.*—Usually 1.

*Generally.*—Average in size.

*Length.*—Approximately 20.0 to 22.0 millimeters including the ovary, which has a size of approximately 1.5 to 2.0 millimeters. Generally, pistil's length is equal to or higher than filaments' length, sometimes slightly smaller.

*Color.*—Considered a very pale green (RHS Yellow Green 150 D or RHS Yellow Green 151 D). The color evolves during the blooming.

*Surface texture.*—Non pubescent.

FRUIT

Maturity when described: Very firm ripe condition (shipping ripe).

Date of first picking: Jun. 29, 2003.

Date of last picking: The date of harvest varies slightly with the prevailing climatic conditions. The 'NECTAFUN variety has a medium date of picking, and a grouped maturity. The maturity is grouped within 10 to 14 days and the harvest is generally performed in two runs. Last known picking times begin Jun. 22, 2007; then Jun. 17, 2008; then Jun. 28, 2009; then Jul. 5, 2010; then Jun. 15, 2011.

Size:

*Generally.*—Homogeneous in size.

Average cheek diameter: Approximately 70.0 to 80.0 millimeters.

Average axial diameter: Approximately 69.0 to 74.0 millimeters.

Typical weight: Generally about 200.0 to 250.0 grams. This characteristic is highly dependent upon the prevailing cultural practices, and therefore is not particularly distinctive of the variety.

Fruit form:

*Generally.*—Round. The fruit is generally uniform in symmetry, viewed from the suture's plane.

Fruit suture: Wide-mouthed and slightly marked, extending from the base to the apex. No apparent callousing or stitching exists along the suture line. Not pointed.

Suture:

*Color.*—The suture has generally a similar color to the whole fruit color, a homogenous purple red (RHS Greyed Purple 185 A or Orange Red Group N 34 A).

Ventral surface:

*Form.*—Smooth.

Apex: Non-prominent, generally slightly depressed.

Base: Semi-flared, shallow.

Stem cavity: Average depth of the stem cavity is about 8.0 millimeters. Average width is about 12.0 to 14.0 millimeters.

Fruit skin:

*Thickness.*—Considered very thick and strong, and the adherence of skin to flesh is strong.

*Texture.*—Glabrous.

*Taste.*—Semi-sweet, aromatic, with a high level of sugars.

*Tendency to crack.*—None observed.

Color:

*Blush color.*—This blush color is a luminous red (RHS Greyed Purple 185 A or RHS Orange Red Group N 34 A). The red blush covers 60% to 80% of the fruit skin surface on a orange background (RHS Orange Red Group 34 B to 34 C). The percentage of the blush on the fruit skin surface can vary, and is generally dependant upon the prevailing conditions under which the fruit was grown.

*Ground color.*—The ground color covers 20% to 40% of the fruit skin surface, and is considered orange (RHS Orange Red Group 34 B to 34 C).

Fruit stem: Medium in length, approximately 8.0 millimeters.

Diameter: Approximately 3.0 to 4.0 millimeters.

Color: Pale green (RHS Yellow Green 145A to 145 B).

Flesh:

*Ripens.*—Very evenly, homogenously, slowly.

*Texture.*—Very firm, very dense, crunchy, melting, juicy at harvest maturity stage.

*Fibers.*—Not fibrous.

*Aroma.*—Pronounced.

*Eating quality.*—Considered very good and with a high level of sugars.

*Flavor.*—Considered semi-sweet and very aromatic. The Brix is generally superior to 13 degrees and acidity comprised between 5 and 9 meq/100 ml.

*Juice.*—Very juicy at complete maturity.

*Brix.*—Generally superior to 13.0 degrees. This characteristic varies slightly with the number of fruit per tree; prevailing cultural practices; and the surrounding climatic conditions.

*Flesh color.*—Orange yellow flesh (RHS Yellow Orange 16 C) usually with red pigmentation (RHS Red 53 A) in the stone cavity and around the stone cavity, where the pigmentation is star shaped on approximately 10.0 millimeters.

STONE

Type: Clingstone.

Size: Considered medium for the variety. The stone size varies significantly depending upon the tree vigor, crop load and prevailing growing conditions.

Length: Approximately 32.0 millimeters.

Width: Approximately 23.0 millimeters.

Diameter: Approximately 17.0 to 20.0 millimeters.

Form: Elliptic.

Base: Straight.

Apex:

*Shape.*—The stone apex is short, pointed.

Stone Cavity: Considered medium size, with an ovate-form and dimensions corresponding to the stone's dimensions.

Stone surface:

*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

Ventral edge:

*Width.*—Considered small to medium, and having a dimension of approximately 2.0 millimeters at mid-suture.

Dorsal edge:

*Shape.*—Grooved, sometimes largely grooved.

Stone color: The color of the dry stone is generally considered orange (RHS Greyed Orange 170 C to 170 D or RHS Greyed Purple 184 B to 184 C).

Tendency to split: Splitting is absent, depending on climatic conditions between blooming period and stone hardening.

Kernel:

*Size.*—The kernel is considered medium.

*Length.*—Approximately 19.0 millimeters.

*Width.*—Approximately 10.0 millimeters.

*Thickness.*—Approximately 4.0 millimeters.

*Form.*—Considered oblate and elliptic.

*Pellicle.*—Pubescent.

*Color.*—The kernel skin is a orange-brown (RHS Greyed Orange N 170 A or RHS Greyed Orange 166 A to 166 C). The almond, which is the seed of the kernel, is cream-white (RHS Orange White 159 B). The kernel and its embryo are mature at the time of fruit maturity.

Use: The subject variety 'NECTAFUN is considered to be a nectarine tree of the medium season of maturity, and which produces fruits that are considered firm, attractively colored and very luminous. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruit have a slow maturation and a long shelf life both on the tree after growth completion and after harvesting without alteration. After harvest, fruits are well preserved more than 4 weeks at 2.0 degree Celsius.

Shipping quality: Considered very good. The fruit of the new yellow nectarine variety showed minimal bruising of the flesh or skin damage after being subjected to normal harvesting and packing procedures. Its resistance to handling during harvest and packing and its long shelf life without alteration after harvest easily permit 3 weeks to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of yellow nectarine tree as illustrated and described, characterized by fruits with high eating quality and very long shelf life without alteration before and after harvesting, with a semi-sweet orange yellow flesh, with red pigmentation, and an attractive luminous skin with a high percentage of red blush on skin surface.

* * * * *